(12) United States Patent
Krugman et al.

(10) Patent No.: US 10,321,962 B2
(45) Date of Patent: *Jun. 18, 2019

(54) METHOD FOR VOLUME DETERMINATION AND GEOMETRIC RECONSTRUCTION

(71) Applicant: COVIDIEN LP, Mansfield, MA (US)

(72) Inventors: Kimberly A. Krugman, Boulder, CO (US); Casey M. Ladtkow, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/480,685

(22) Filed: Apr. 6, 2017

(65) Prior Publication Data

US 2017/0209220 A1 Jul. 27, 2017

Related U.S. Application Data

(63) Continuation of application No. 12/260,811, filed on Oct. 29, 2008, now Pat. No. 9,622,813.
(Continued)

(51) Int. Cl.
*A61B 34/10* (2016.01)
*A61B 5/055* (2006.01)
(Continued)

(52) U.S. Cl.
CPC ............. *A61B 34/10* (2016.02); *A61B 5/055* (2013.01); *A61B 6/032* (2013.01); *A61B 6/037* (2013.01);
(Continued)

(58) Field of Classification Search
CPC . A61B 5/055; A61B 18/1206; A61B 18/1477; A61B 34/10; A61B 8/481;
(Continued)

(56) References Cited

U.S. PATENT DOCUMENTS 3,631,363 A 12/1971 Miller
4,397,313 A 8/1983 Vaguine
(Continued)

FOREIGN PATENT DOCUMENTS

DE 390937 C 3/1924
DE 1099658 B 2/1961
(Continued)

OTHER PUBLICATIONS

Frank Lindseth, thesis, Ultrasound Guided Surgery: Multimodal Visualization and Navigation Accuracy, Norwegian University of Science and Technology, Dec. 2002.*
(Continued)

*Primary Examiner* — Bo Joseph Peng

(57) ABSTRACT

A method for determining a volume of ablated tissue includes the steps of supplying energy to tissue, indicating an axis within the tissue, and simulating slicing of the tissue substantially perpendicular to the axis to obtain a plurality of simulated slices. Each of the plurality of simulated slices has a thickness, a cross-sectional perimeter, and a trajectory point defined by the axis within the tissue. The method further includes the steps of determining a volume of each of the plurality of simulated slices based on the trajectory point, the cross-sectional perimeter, and the thickness of each simulated slice, and summing the volumes from each of the plurality of simulated slices to obtain the volume of the ablated tissue.

7 Claims, 4 Drawing Sheets

Related U.S. Application Data

(60) Provisional application No. 60/984,605, filed on Nov. 1, 2007.

(51) Int. Cl.
*A61B 18/12* (2006.01)
*A61B 18/14* (2006.01)
*A61B 6/03* (2006.01)
*A61B 8/08* (2006.01)
*A61B 6/12* (2006.01)
*A61B 6/00* (2006.01)
*A61B 17/00* (2006.01)
*A61B 18/00* (2006.01)
*A61B 90/00* (2016.01)

(52) U.S. Cl.
CPC ............ *A61B 8/0841* (2013.01); *A61B 8/481* (2013.01); *A61B 18/1206* (2013.01); *A61B 18/1477* (2013.01); *A61B 6/12* (2013.01); *A61B 6/4488* (2013.01); *A61B 2017/00106* (2013.01); *A61B 2018/00011* (2013.01); *A61B 2018/00577* (2013.01); *A61B 2018/00738* (2013.01); *A61B 2018/00744* (2013.01); *A61B 2018/00791* (2013.01); *A61B 2034/104* (2016.02); *A61B 2090/378* (2016.02); *A61B 2090/3782* (2016.02); *A61B 2090/3925* (2016.02)

(58) Field of Classification Search
CPC ....... A61B 8/0841; A61B 6/037; A61B 6/032; A61B 6/12; A61B 6/4488; A61B 2017/00106; A61B 2018/00011; A61B 2018/00738; A61B 2018/00577; A61B 2018/00744; A61B 2018/00791; A61B 2090/3782; A61B 2090/378; A61B 2090/3925; A61B 2034/104
See application file for complete search history.

(56) References Cited

U.S. PATENT DOCUMENTS

| | | |
|---|---|---|
| 4,462,412 A | 7/1984 | Turner |
| 4,572,190 A | 2/1986 | Azam et al. |
| 4,798,215 A | 1/1989 | Turner |
| 5,097,844 A | 3/1992 | Turner |
| 5,230,623 A | 7/1993 | Guthrie et al. |
| 5,409,006 A | 4/1995 | Buchholtz et al. |
| 5,417,210 A | 5/1995 | Funda et al. |
| 5,588,432 A | 12/1996 | Crowley |
| 5,704,355 A | 1/1998 | Bridges |
| 5,943,719 A | 8/1999 | Feldman et al. |
| 6,031,375 A | 2/2000 | Atalar et al. |
| 6,241,725 B1 | 6/2001 | Cosman |
| 6,375,606 B1 | 4/2002 | Garibaldi et al. |
| 6,451,015 B1 | 9/2002 | Rittman, III et al. |
| 6,478,793 B1 | 11/2002 | Cosman et al. |
| 6,506,189 B1 | 1/2003 | Rittman, III et al. |
| 6,530,922 B2 | 3/2003 | Cosman et al. |
| 6,575,969 B1* | 6/2003 | Rittman ............. A61B 18/1482 128/898 |
| 6,603,994 B2 | 8/2003 | Wallace et al. |
| 6,725,080 B2 | 4/2004 | Melkent et al. |
| 6,881,214 B2 | 4/2005 | Cosman et al. |
| 7,282,049 B2 | 10/2007 | Orszulak et al. |
| 7,429,262 B2 | 9/2008 | Woloszko et al. |
| 7,439,736 B2 | 10/2008 | Meaney et al. |
| 7,467,015 B2 | 12/2008 | van der Weide |
| 7,480,533 B2 | 1/2009 | Cosman et al. |
| 7,565,207 B2 | 7/2009 | Turner et al. |
| 7,642,451 B2 | 1/2010 | Bonn |
| 7,875,024 B2 | 1/2011 | Turovskiy et al. |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |
| 8,216,227 B2 | 7/2012 | Podhajsky |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,292,880 B2 | 10/2012 | Prakash et al. |
| 8,292,881 B2 | 10/2012 | Brannan et al. |
| 8,343,149 B2 | 1/2013 | Rossetto et al. |
| 8,353,902 B2 | 1/2013 | Prakash |
| 8,353,903 B2 | 1/2013 | Podhajsky |
| 8,394,086 B2 | 3/2013 | Behnke et al. |
| 8,435,237 B2 | 5/2013 | Bahney |
| 8,463,396 B2 | 6/2013 | Podhajsky |
| 8,512,328 B2 | 8/2013 | Rossetto et al. |
| 8,834,409 B2 | 9/2014 | Manley |
| 8,834,460 B2 | 9/2014 | Peterson |
| 8,945,111 B2 | 2/2015 | Brannan et al. |
| 8,965,536 B2 | 2/2015 | Bonn et al. |
| 9,113,924 B2 | 8/2015 | Brannan et al. |
| 9,173,706 B2 | 11/2015 | Rossetto |
| 9,198,723 B2 | 12/2015 | Paulus et al. |
| 9,271,796 B2 | 3/2016 | Buysse et al. |
| 9,277,969 B2 | 3/2016 | Brannan et al. |
| 9,375,272 B2 | 6/2016 | Rossetto et al. |
| 9,622,813 B2 | 4/2017 | Krugman et al. |
| 2002/0022836 A1 | 2/2002 | Goble et al. |
| 2003/0000535 A1* | 1/2003 | Galloway, Jr. ......... A61B 90/36 128/898 |
| 2003/0032951 A1 | 2/2003 | Rittman et al. |
| 2004/0097805 A1 | 5/2004 | Verard et al. |
| 2004/0242992 A1 | 12/2004 | Hareyama |
| 2005/0113651 A1* | 5/2005 | Wood ................. G06F 19/3437 600/300 |
| 2005/0197568 A1 | 9/2005 | Vass et al. |
| 2006/0052690 A1 | 3/2006 | Sirohey et al. |
| 2006/0079887 A1 | 4/2006 | Buysse et al. |
| 2007/0250054 A1 | 10/2007 | Drake |
| 2008/0021448 A1 | 1/2008 | Orszulak et al. |
| 2009/0248005 A1 | 10/2009 | Rusin et al. |
| 2010/0030206 A1 | 2/2010 | Brannan et al. |
| 2010/0030210 A1 | 2/2010 | Paulus |
| 2010/0045559 A1 | 2/2010 | Rossetto |
| 2010/0076422 A1 | 3/2010 | Podhajsky |
| 2010/0087808 A1 | 4/2010 | Paulus |
| 2010/0262134 A1 | 10/2010 | Jensen et al. |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |

(56) References Cited

FOREIGN PATENT DOCUMENTS

| | | |
|---|---|---|
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 246350 A1 | 11/1987 |
| EP | 0481685 A1 | 4/1992 |
| EP | 0521264 A2 | 1/1993 |
| EP | 556705 A1 | 8/1993 |
| EP | 0558429 A1 | 9/1993 |
| EP | 0572131 A1 | 12/1993 |
| EP | 0541930 B1 | 3/1998 |
| EP | 836868 A2 | 4/1998 |
| EP | 1278007 A1 | 1/2003 |
| EP | 1159926 A3 | 3/2003 |
| EP | 1645234 A1 | 4/2006 |
| EP | 1810627 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| SU | 166452 | 1/1965 |
| SU | 401367 A1 | 10/1973 |
| SU | 727201 A2 | 4/1980 |
| WO | 9634571 A1 | 11/1996 |
| WO | 9741924 A1 | 11/1997 |
| WO | 9743971 A2 | 11/1997 |
| WO | 9904704 A2 | 2/1999 |
| WO | 9904710 A1 | 2/1999 |
| WO | 9966834 A1 | 12/1999 |
| WO | 0048672 A1 | 8/2000 |
| WO | 0051513 A1 | 9/2000 |
| WO | 0101847 A1 | 1/2001 |
| WO | 0174252 A2 | 10/2001 |
| WO | 0245790 A2 | 6/2002 |
| WO | 2002061880 A2 | 8/2002 |
| WO | 2004/112628 A1 | 12/2004 |
| WO | 2005016119 A2 | 2/2005 |

OTHER PUBLICATIONS

Lazebnik et al., Sub-acute Changes in Lesion Conspicuity and Geometry Following MR-guided Radiofrequency Ablation, Journal of Magnetic Resonance Imaging 18:353-359 (2003).*

LigaSure.™. Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure.™. Vessel Sealing System and LigaSure.™. Atlas 20 cm Open Instrument" Innovations That Work, Jun. 2003.

Muller et al., "Extended Left Hemicolectomy Using the LigaSure. ™. Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thennoradiotheray and Thermochemotherapy (1995) vol. I, Biology, Physiology, Physics, pp. 279-320.

Palazzo et al., "Randomized clinical trial of LigaSure.™. versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, OApr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

(56) References Cited

OTHER PUBLICATIONS

Rothenberg et al., "Use of the LigaSure.™. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
5. Humphries Jr. et al., "Finite.cndot.Element Codes to Model Electrical Heating and Non.cndot.LInear Thermal Transport in Biological Media", Proc. ASME HTD-355, 131 (1997).
Urologix, Inc.-Medical Professionals: Targis.™. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.™. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Butz et al., Pre- and Intra-operative Planning and Simulation of Percutaneous Tumor Ablation, Medical Image Computing and Computer Assisted Intervention,Pittsburgh, USA., Oct. 2000, 317-326.
U.S. Appl. No. 08/483,742, filed Jun. 7, 1995.
U.S. Appl. No. 08/136,098, filed Oct. 14, 1991.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.™. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.™. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.™. Vessel Sealing System in Abdominal Surgery" Innovations That Work, Jun. 2002.

(56) References Cited

OTHER PUBLICATIONS

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.™." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" In William RH, Rengachary SS (eds): Neurosurgery, New York: McGraw-Hill, vol. 111, (1984), pp. 2490-2499.
Crawford et al., "Use of the LigaSure.™. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure.™. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrell et al., "Use of the LigaSure.™. Vessel Sealing System for Peri-Hilar Vessels in Laparoscopic Nephrectomy" Sales/Product Literature 2000.
Johnson, "Evaluation of the LigaSure.™. Vessel Sealing System in Hemorrhoidectormy" American College of Surgeons (ACS) Clinic La Congress Poster (2000).
Johnson, "Use of the LigaSure.™. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.™. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 376-878.

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
Search Report EP 04027314 dated Mar. 31, 2005.
Search Report EP 04027479 dated Mar. 17, 2005.
Search Report EP 04027705 dated Feb. 10, 2005.
Search Report EP 04710258 dated Oct. 15, 2004.
Search Report EP 04752343.6 dated Jul. 31, 2007.
Search Report EP 05002027.0 dated May 12, 2005.
Search Report EP 05002769.7 dated Jun. 19, 2006.
Search Report EP 05013463.4 dated Oct. 7, 2005.
Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
Search Report EP 06024123.9 dated Mar. 6, 2007.
Search Report EP 06025700.3 dated Apr. 12, 2007.
Search Report EP 07000885.9 dated May 15, 2007.
Search Report EP 07001480.8 dated Apr. 19, 2007.
Search Report EP 07001481.6 dated May 2, 2007.
Search Report EP 07001485.7 dated May 23, 2007.
Search Report EP 07001488.1 dated Jun. 5, 2007.
Search Report EP 07001489.9 dated Dec. 20, 2007.
Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.

(56) References Cited

OTHER PUBLICATIONS

European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.

* cited by examiner

METHOD FOR VOLUME DETERMINATION AND GEOMETRIC RECONSTRUCTION

CROSS-REFERENCE TO RELATED APPLICATIONS

This application is a continuation of U.S. patent application Ser. No. 12/260,811 filed on Oct. 29, 2008, which claims priority to U.S. Provisional Patent Application No. 60/984,605 filed on Nov. 1, 2007, the entire contents of each of which are incorporated herein by reference.

BACKGROUND

1. Technical Field

The present disclosure relates to electrosurgical apparatuses, systems and methods. More particularly, the present disclosure is directed to a system and method for determining the volume of an ablation lesion during and/or after a tissue ablation procedure utilizing electrosurgical electrodes and imaging means.

2. Background of Related Art

Energy-based tissue treatment is well known in the art. Various types of energy (e.g., electrical, ultrasonic, microwave, cryo, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In the case of tissue ablation, high radio frequency electrical current is applied to a targeted tissue site to create an ablation volume. The resulting ablation volume may then be observed and various ablation metrics may be measured and recorded. Conventional methods of obtaining ablation metrics include recording the small diameter, large diameter, and height of the ablated tissue to calculate the volume. Typically, these three parameters are input for the equation for ellipsoidal volume to calculate an approximate ablation volume. Conventional methods such as this often provide inexact measurements, inconsistent recordings, as well as inaccurate reporting of achieved volumes. Further, conventional methods of volumetric calculation lack evaluative tools such as determining the effect of adjacent structures on the ablation volume, qualifying the completeness of the ablation volume, predicting specific volumes and/or shapes based on a given energy applicator configuration.

SUMMARY

The present disclosure elates to a method for determining a volume of ablated tissue. In a first step, energy is supplied to tissue. In a second step, an axis within the tissue is indicated. In a third step, a simulated slicing of the tissue substantially perpendicular to the axis is performed to obtain a plurality of simulated slices. Each of the plurality of simulated slices has a thickness, a cross-sectional perimeter, and a trajectory point that is defined by the axis. In a fourth step, a volume of each of the plurality of simulated slices is determined based on the trajectory point, the cross-sectional perimeter, and the thickness of each simulated slice. In a fifth step, the volumes from each of the plurality of simulated slices are summed to obtain the volume of the ablated tissue.

According to another embodiment of the present disclosure, an electrosurgical system includes an electrosurgical generator coupled to one or more electrodes configured to be inserted into a portion of tissue. The electrode(s) is further configured to supply electrosurgical energy to the portion of tissue to create an ablation volume. The system further includes a feedback unit coupled to an imager for imaging the portion of tissue to obtain a graphical scan of the ablation volume and the electrode(s). A controller marks an axis of the electrodes within the graphical scan. The controller is further configured to simulate slicing the graphical scan substantially perpendicular to the axis to obtain a plurality of simulated slices. Each of the plurality of simulated slices has a thickness, a cross-sectional perimeter, and a trajectory point defined by the axis of the electrode(s). The controller is further configured to determine a volume of each of the plurality of simulated slices based on the trajectory point, the cross-sectional perimeter, and the thickness of each simulated slice and further, to sum the volumes from each of the plurality of simulated slices to determine the ablation volume.

According to yet another embodiment the present disclosure, a method of storing a library of ablation data related to the use of a treatment device includes a first step of providing a treatment device having a particular configuration. In a second step, electrosurgical energy is supplied to the treatment device for application to tissue to generate a plurality of feedback parameters based on the particular configuration of the treatment device. In a third step, an imaging device is provided for imaging tissue to create one or more images corresponding to the plurality of feedback parameters based on the particular configuration of the treatment device. The imaging device is configured to communicate with a feedback unit for storing the library of ablation data. In a fourth step, the image(s) and the plurality of feedback parameters are stored in the library of ablation data for subsequent retrieval. The image(s) and the plurality of feedback parameters correspond to the particular configuration of the treatment device applied to tissue. In a fifth step, a completeness factor is determined based on deviations between the image(s) corresponding to feedback parameters based on the particular configuration of the treatment device and ablation data stored in the library corresponding to feedback parameters generated by application to tissue of a treatment device having substantially the same configuration.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for a system and method for determining a volume of an ablation lesion and providing a geometric reconstruction of the ablation volume. The ablation lesion may be created by applying any suitable energy, such as radiofrequency ("RF"), microwave, electrical, ultrasound, heat, cryogenic, and laser. For the purposes of illustration, the following description assumes the application of RF energy to create ablation lesions in accordance with embodiments of the present disclosure.

Figure 1A:
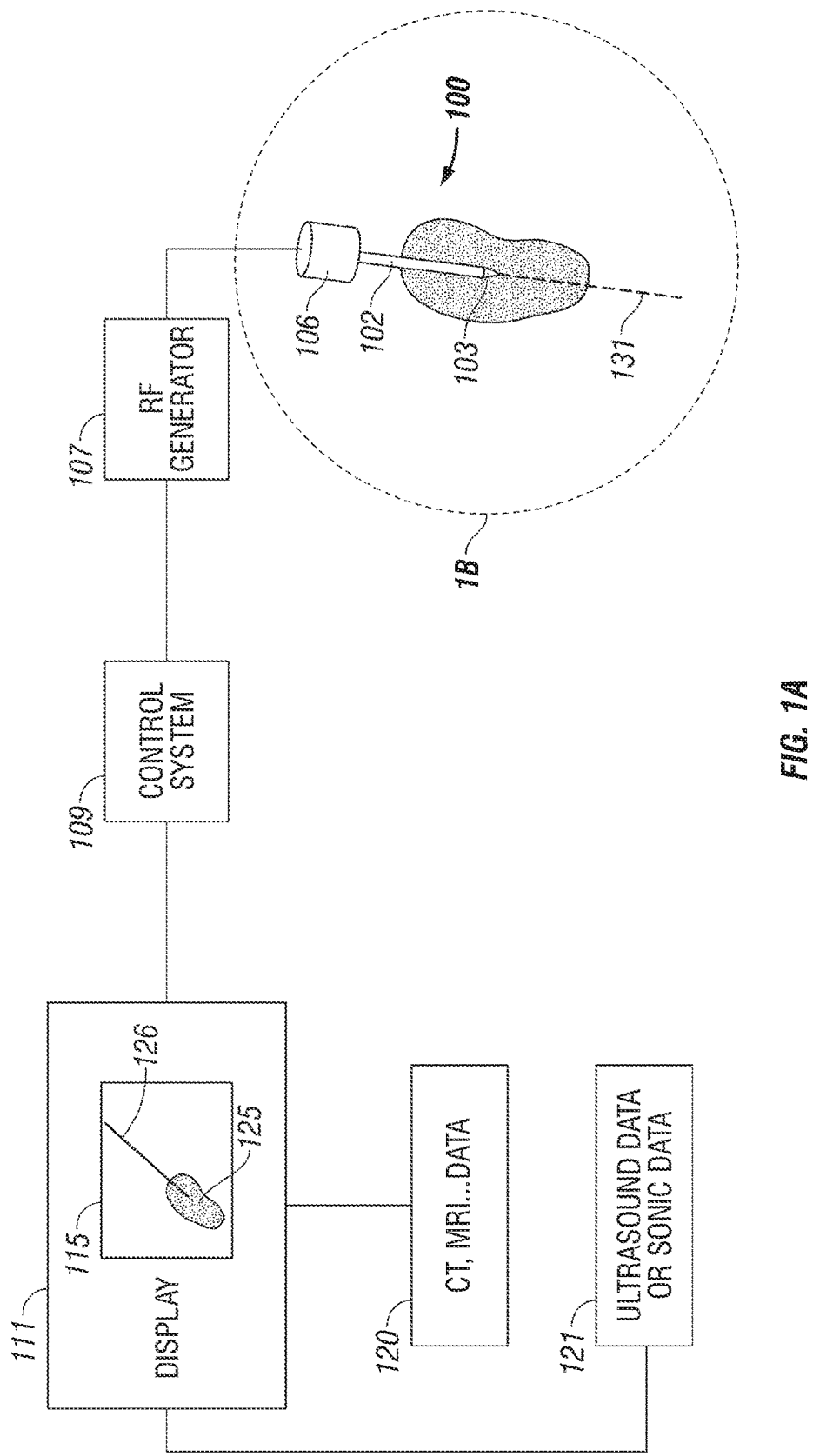
FIG. 1A shows an electrosurgical system for tissue ablation, measuring ablation volume, and displaying image scan data according to one embodiment of the present disclosure.

Referring to FIG. 1A, an ablation electrode 100 is shown having an insulated shaft 102 and an electrically exposed tip 103. Electrode 100 may be, for example, a high frequency or RI thermo-ablation electrode configured to be placed in the body of a patient (not explicitly shown) so that the tip 103 is near a target volume, such as a cancerous tumor or other tissue structure within the body. A hub or junction connector element illustrated schematically by 106 may be any type of connection device such as jacks, hoses, ports, etc. that connect the RF electrode to a power source, such as a radiofrequency (RF) generator 107. The generator 107 according to an embodiment of the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes suitable electronic circuitry configured for generating radio frequency power specifically suited for various electrosurgical modes (e.g., cutting, blending, division, etc.) and procedures (e.g., monopolar, bipolar, vessel sealing, tissue ablation).

Also shown is a control system 109 coupled to generator 107, which may be a computer, a microprocessor, or an electromechanical device configured to receive RF energy input parameters from RF generator 107, such as power, current, voltage, energy, time, impedance, etc. In some embodiments, a coolant supply system (not explicitly shown) may also be included, for example, in operative cooperation with RF generator 107 and/or incorporated within RF generator 107. The coolant supply system is configured to output various feedback parameters such as temperature, multiple temperatures at different points, and the like into the control system 109. The coolant supply system parameters can then be used as feedback control input parameters. Based on one or more of these parameters, the control system 109 modulates, moderates, or otherwise monitors output response at the generator 107.

Also shown in FIG. 1 is a computer system 111, which may be, for example, a PC or computer graphic workstation. The computer system 111 is coupled to the control system 109. Computer system 111 processes the parameters of the RF generator 107 and coolant supply system (not explicitly shown) plus other geometric parameters regarding the electrode as well as image scan data taken before, during or after thermo-surgery. Computer system 111 assimilates all of these parameters and displays them in various representations, digital representations, and analog meter type representations, as an interface to the operator or controller of the processor during the preplan process or during the process of ablation heating itself. In one embodiment, image data 120 might represent image scan data from such image scanners such as from CT, MRI, PET, or other tomographic or X-ray, plain film, or digitized image scan data. That data may be stored in the computer system 111 and be represented as an array of raw data, slices, reconstructed slices, three-dimensional renderings, "slice and dice" three-dimensional or two-dimensional renderings, contoured or segmented anatomical structures, color rendered, differentiated structures, both pathological and normal so that the surgeon may substantially visualize the anatomy and pathology of the patient prior to, during, or after the procedure. Data from CT or MRI may be taken days or even months prior, and could be put into stereotactic or non-stereotactic space, for example, by utilizing any suitable imaging software and/or image processing software in conjunction with one or more graphic references or other suitable marking systems or software.

Image data 121 may represent ultrasound scan data or sonic monitoring data such as from a sonic detector system that can visualize before, during, and after the thermosurgery procedure the course of the electrode in the body, electrode position with respect to anatomy, and even the process of the heating mechanism and result thereof. This data could also be fed into computer system 111 and represented in various ways alternatively on a graphics display screen. Image data 121 may be stored in computer system 111 to correspond with particular configurations of electrode 100, such as, for example, geometric parameters of the electrode tip 103. In this manner, a library of feedback data may be stored in computer system 111 and indexed according to particular configurations of the electrode, thereby assisting the surgeon in predicting future ablation results for a given electrode configuration. Further, there may be calculation algorithms, look-up tables, heuristic algorithms, historical clinical data, etc. that can be used in a preplan setting and displayed, implemented, overlaid, and used to control the image data, course of RF generator output, as well as the control system to tailor or preplan the results of the ablation that can be visualized again on the computer system 111 and further computed and stored therein.

Computer system 111 includes a display 115 for outputting image data 120 and 121, such as the real-time or preplanned trajectory of a probe path 126 and electrode tip as the tip 126 is inserted into the body and/or a tumor structure represented by a cloud of dots 125. This might also be, for example, the display from an ultrasonic, CT, or MRI scanner that actually visualizes the probe 126 and a tumor 125 or a profused volume corresponding to the destructive ablation volume, perhaps represented or visualizable as volume 125. Use of CT contrast agents or dyes can be used to mark the ablation volume following ablation, and this can give a direct view of the results immediately following the heating process.

Display 115 may also be configured to show a preplanned path of an electrode in a particular slice or reconstructed slice plane of volumetric rendering in a three-dimensional aspect (not explicitly shown), and also configured to show isotherm surfaces or intersected surfaces or isotherm lines (not explicitly shown), which might represent a preplan or a calculation of the ablation volume around the tip of the electrode. Display 115 may also be configured to show a view, slice, or reconstructed slice, and within it a preplanned or actual plan or post-thermosurgery path representing the approach of a thermosurgical probe 100 into the patient's anatomy to achieve a target volume that might be seen on that image slice such as for example a tumor as seen on image data 120 and 121.

Volumetric calculations for ablation volumes may be determined from cross-sectional perimeters of slices of a target tissue site and/or block of tissue and subsequently reconstructed and graphically represented in a 2-D and/or 3-D manner on display 115, as will be discussed in further detail below.

Figure 1B:
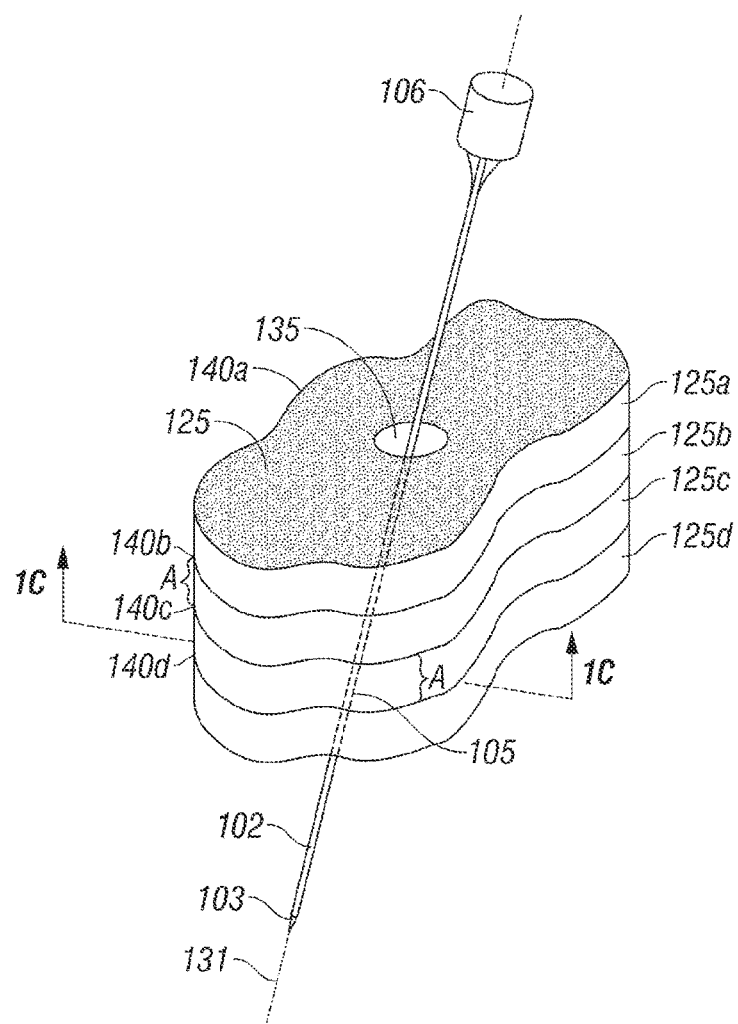
FIG. 1B shows an electrode defining a path through tissue for heating ablation according to one embodiment of the present disclosure.
Figure 1C:
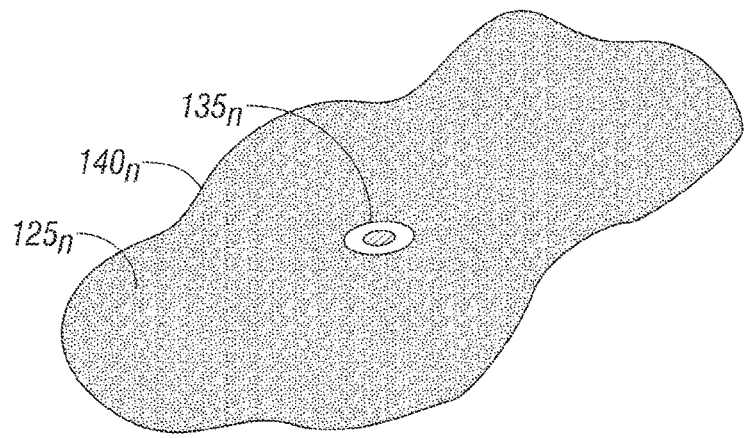
FIG. 1C shows a sliced segment of the tissue of FIG. 1B.

Turning now to FIG. 1B, a trajectory or path 131 of electrode 100 through ablation volume 125 is shown. Path 131 may also be defined as an axis of electrode 100 through ablation volume 125. Electrode 100 is used to create an ablation lesion at a targeted site such as volume 125 by heating tissue via application of RF energy from the generator 107 to the tissue. Path 131 of electrode 100 through volume 125 provides a trajectory reference or point 135 from which volumetric calculations may be made for volume 125, as will be discussed in further detail below. Volume 125 may be deconstructed into a plurality of slices, depicted here as 125a, 125b, 125c, and 125d, for enabling volumetric determination of volume 125 and, further, graphical representation in display 115, FIG. 1C shows a cross-sectional view of any slice 125n of the plurality of slices 125a-d indicated by line 1C-1C in FIG. 1B. Each of the plurality of slices 125 *n* defines a cross-sectional perimeter 140n generally concentric about trajectory point 135n.

In one embodiment of the present disclosure, the reconstructed graphical representation is fitted to a specific geometry (e.g., ellipsoidal, spherical, etc.) for viewing on display 115. For example, Euclidean distances between perimeter 140 of volume 125 and the perimeter of a pre-specified geometry may be minimized to fit volume 125 to the pre-specified geometry. In this manner, valuable feedback may be provided to a surgeon on the consistency and/or the predictability of the ablation volume achieved based on given energy applicator configurations (e.g., electrode size, electrode tip geometry, etc.). The graphical representation of the reconstructed ablation also allows the surgeon to qualify the completeness or a completeness factor of the ablation lesion achieved based on geometrical similarity between the lesion and any one or more of a particular preplanned geometry provided, for example, by the control system 109. The graphical representation of the reconstructed ablation may also be used to determine the impact from adjacent structures such as, for example, other electrodes, lungs, bones, vessels, tissue extraneous to the present procedure, etc. on a given ablation, as will be discussed in further detail below.

A method for volumetric determination of an ablation volume for subsequent geometric reconstruction and graphical representation according to embodiments of the present disclosure will now be described with reference to FIG. 2 in conjunction with FIGS. 1B and 1C.

In step 300, electrosurgical energy is supplied from the RF generator 107 to the electrode 100. As illustrated in FIG. 1B, electrode 100 is used to create an ablation lesion by heating volume 125 via application of RF energy from the generator 107 to volume 125.

In step 310, path or trajectory 131 of electrode 100 through a target site such as, for example, volume 125 (FIG. 1B) is indicated. Path 131 of electrode 100 through volume 125 defines trajectory point 135 therethrough relative to perimeter 140 of tissue block 125. Trajectory point 135 may be substantially defined through the center of mass of tissue block 125. Trajectory 131 and/or trajectory point 135 may be marked with CT contrast agents or dyes following ablation, giving a direct view of the results immediately following the heating process.

In step 320, volume 125 is cut or "sliced" substantially perpendicular to trajectory point 135 into a plurality of slices 125a-d. Slices 125a-d may be obtained via an image scanner such as, for example, CT, MRI, PET, or other tomographic or X-ray, plain film, or digitized image scan data for subsequent 2D or 3D graphical representation. In this manner; various dimensions and/or measurements of each of the plurality slices 125a-d may be indicated such as, for example, thicknesses, volume, cross-sectional perimeter, etc. for each of the plurality of slices.

In step 330, a thickness, indicated in FIG. 1B as A, and a cross-sectional perimeter 140a-d for each of the plurality of slices 125a-d is determined. Cross-sectional perimeters 140a-d for each of the plurality of slices 125a-d may be derived, for example, from scan data 121 in the computer system 111 such as post-ablation MR images that may or may not include CT contrast agent. Other embodiments of the present disclosure may include deriving from a measurement taken using conventional means such as, for example, dial calipers, slide calipers, digital calipers, electronic calipers, or the like.

In step 340, the volume of each of the plurality of slices 125a-d is determined. Any suitable method for determining volume may be used such as, for example, the contour or perimeter method. This method utilizes each slice of volumetric data individually and models the shape of the volume as defined on each slice. For example, cross sectional perimeter 140a-d for each slice 125a-d may be used to determine the volume using such method. Alternatively, for each slice 125n, thickness A may be multiplied by the perimeter area of that particular slice to determine the slice volume. This determination is carried out for each of the plurality of slices 125a-d.

In step 350, the volume determinations derived in step 340 for each of the plurality of slices 125a-d are summed to yield an ablation volume. In this manner, an accurate volumetric determination is made rather than approximated calculations yielded by conventional and/or presently competing volumetric calculation methods.

Figure 2:
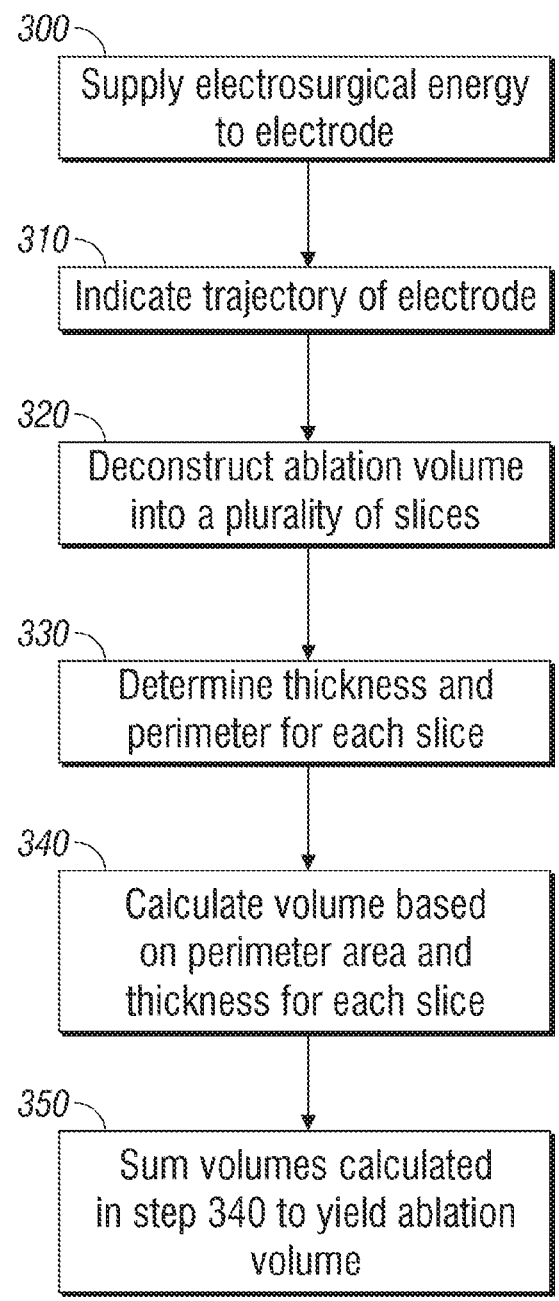
FIG. 2 illustrates a method for determining an ablation volume according to embodiments of the present disclosure.
Figure 3:
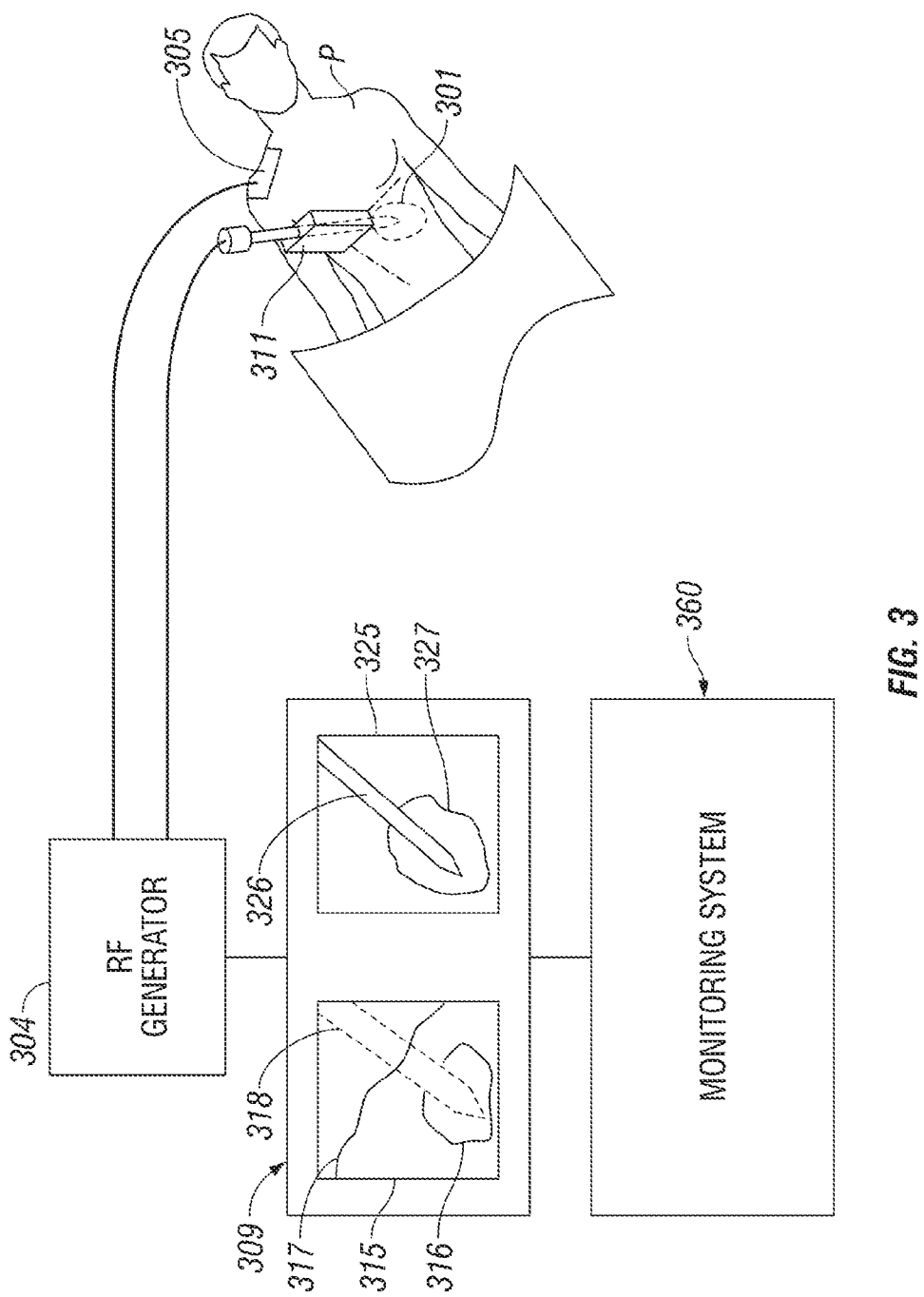
FIG. 3 shows an electrosurgical system for tissue ablation, measuring ablation volume, and displaying image scan data according to another embodiment of the present disclosure.

Referring now to FIG. 3 in conjunction with FIGS. 1B, 1C, and 2, a patient's body is represented schematically by element P, and there is a target volume represented by the dashed line 301. A thermosurgery probe 302 is inserted into the patient's body such that the tip of the probe 303 is placed within the target volume 301. Attached to or in conjunction with or cooperatively coupled with the probe (or probes) 302 is an imaging device 311 which, when placed against the surface of the patient's skin or an organ within the patient's body, images a portion of the patient's body P, including the probe 302 and the target volume 301 or the environment around these elements.

The radiofrequency, laser, high frequency, or other power generator is represented by 304, and in the case of a high frequency generator, a reference electrode 305 is attached to the patient's body around the shoulder region is shown in FIG. 3. The reference electrode 305 might be a gel pad, large area, conductive pad or other type of standard reference electrode that is used in electrosurgery. The imaging device 311 is connected to a monitoring circuit or controller system 360 that can be used to image, analyze, filter, and monitor the image scan data or the like which is received from the imaging device 311. This system 360 may also involve a power source and processor for the imaging device 311. The system 360 includes a feedback unit 309 configured to control monitoring, preplanning, and/or imaging of an ablation area. Feedback unit 309 includes at least one display 315 and/or 325 configured to graphically display 2D or 3D image data. For example, in display 315 there may be represented in 2D or 3D slice or volume representations, image scan data taken from an image scanner such as CT, MR, PET, or ultrasound prior to, during, or after the thermal ablation. In this instance, a patient's skin 317 is defined, a target volume (e.g., tumor 316) is shown, and in the dashed line is a preplanned probe path 318 for a thermal ablation high frequency electrode (e.g., probe 326). By means of such visualization, the probe path 318 can be manipulated within the image or image stack of CT or MR slices, and an optimal path for placement can be achieved. This path could be achieved by criterion from the surgeon such as bringing the probe path along a principal axis of the tumor 316 or from a direction that avoids some critical structures such as arteries, lung, optic nerve, neural structures, etc. Thus, based on image scan data taken from the imaging device 311 prior to the thermal ablation, the surgeon can do a preplanned study and decide on the optimal positioning of the probe 326.

On the display 325 is shown a real-time representation of the probe 326 as it is inserted into the patient's body. The margin 327 may be a reconstruction, either theoretical or actual, of the result of the RF heat ablation. For example, if the window represents an ultrasonic reconstruction, this could be a theoretically generated graphic representation within a preplanned ultrasonic slice direction and probe direction to show what the ecogenic or ultrasonic image would look like when particular cooled tip RF, generator parameters are invoked or used. This window may alternatively represent real-time image data from the CT or MR or other type of scanning means, if the patient is within such a scanner during the RF heating process. The window may also represent the changes or modifications or digitally subtracted differential changes of the tissue volume as a result, directly or indirectly, of the ablation isotherms. Thus, one may visualize directly the effect of heating on the patients tissue, and this may be displayed in such a window. There may be a superposition of a preplanned or prescanned tumor volume, as compared to the actual volume of the tumor at the time of surgery or the ablation volume as one detects it during surgery.

Direct detection of changes in the physiology as a result of the heating to gauge the extent of the ablation volume can be done by ultrasound, CT, MRI, PET, and other imaging modalities, and can be displayed on the display 325 of the feedback unit 309 or, indeed, on the graphics display of the ultrasound or CT, MR, or other scanning machine as supplied by standard manufacturers. Each of these scanning devices has a graphics display on a CRT, liquid crystal, or other means which can display the results of the tomographic or volumetric scanning. These can be used in conjugation with the thermosurgery to evaluate the effect of the thermosurgery itself. Use of ultrasound and standard sonic detection and scanning may be used in conjugation with the thermosurgery to evaluate the effect of the lesion or ablation process.

The entire process of the heating could be preplanned by the operator hours or days before based on the imaging and preplanned calculations of ablation volume with the tip geometry and ablation parameters described with respect to FIG. 1. Thus, system 360 could basically mediate the entire process of supply of RF power from generator 304. Indwelling controllers, electronics, microprocessors, or software may be programmed to govern the entire process or allow preplan parameters by the operator based on his selection of a tip geometry and overall ablation volume as selected according to a tumor or pathological volume to be destroyed. Many variants or interconnections of the block diagram shown in FIG. 3 or additions of said diagram could be devised by those skilled in the art of regulation systems.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for determining a volume of ablated tissue, comprising:
   providing electrosurgical energy to tissue via an ablation device to create an ablated tissue volume;
   generating a trajectory of the ablation device through the ablated tissue volume;
   generating a plurality of image slices of the ablated tissue volume transverse to the trajectory;
   determining, for each of the plurality of image slices of the ablated tissue volume, a surface area of the image slice based on the trajectory of the ablation device relative to a cross-sectional perimeter of the image slice;
   determining, for each of the plurality of image slices of the ablated tissue volume, a volume of the image slice based on the determined surface area of the image slice and a thickness of the image slice; and
   summing the determined volumes of the image slices to determine a volume of the ablated tissue volume.

2. The method according to claim 1, further comprising indicating a trajectory point through the ablated tissue volume based on the trajectory of the ablation device.

3. A method for determining a volume of ablated tissue, comprising:
   providing electrosurgical energy to tissue via an ablation device to create an ablated tissue volume;
   imaging the ablated tissue volume to generate a plurality of image slices of the ablated tissue volume;
   determining, for each of the plurality of image slices of the ablated tissue volume, a surface area of the image slice based on a trajectory of the ablation device relative to a cross-sectional perimeter of the image slice;
   determining, for each of the plurality of image slices of the ablated tissue volume, a volume of the image slice based on the determined surface area of the image slice; and
   summing the determined volumes of the plurality of image slices to determine a volume of the ablated tissue volume.

4. The method according to claim 3, wherein the determined volume for each of the plurality of image slices is based on the determined surface area of the image slice and a thickness of the image slice.

5. A method for determining a volume of ablated tissue comprising:
   providing electrosurgical energy to tissue via an ablation device to create an ablated tissue volume;

imaging the ablated tissue volume transverse to a trajectory of the ablation device through the ablated tissue volume to generate a plurality of image slices of the ablated tissue volume;

determining, for each of the plurality of image slices of the ablated tissue volume, a surface area of the image slice based on the trajectory of the ablation device;

determining, for each of the plurality of image slices of the ablated tissue volume, a volume of the image slice based on the determined surface area of the image slice; and summing the determined volumes from each of the plurality of image slices to obtain the volume of the ablated tissue volume.

6. The method according to claim 5, wherein the determined surface area for each of the plurality of image slices is based on the trajectory of the ablation device relative to a cross-sectional perimeter of the image slice.

7. The method according to claim 5, wherein the determined volume for each of the plurality of image slices is based on the determined surface area of the image slice and a thickness of the image slice.

\* \* \* \* \*